United States Patent [19]
Doyle, Jr. et al.

[11] 3,973,028
[45] Aug. 3, 1976

[54] 1-DIMETHYLCARBAMYL-3-BRANCHED ALKYL-1,2,4-TRIAZOL-5-YL-(N-SUBSTITUTED) SULFONAMIDES AND USE AS INSECTICIDES

[75] Inventors: William C. Doyle, Jr., Leawood; Joel L. Kirkpatrick, Overland Park, both of Kans.

[73] Assignee: Gulf Oil Corporation, Pittsburgh, Pa.

[22] Filed: Oct. 10, 1974

[21] Appl. No.: 513,605

Related U.S. Application Data

[63] Continuation-in-part of Ser. No. 407,678, Oct. 18, 1973, abandoned.

[52] U.S. Cl. ............................. 424/269; 424/226; 424/248; 424/267; 424/DIG. 8; 260/157; 260/247.1 M; 260/293.69; 260/307 F; 260/308 R

[51] Int. Cl.$^2$ ............................................ A01N 9/00
[58] Field of Search ....................... 424/269; 260/308

[56] References Cited
UNITED STATES PATENTS
3,701,784   10/1972   Seidel et al. ........................ 424/269

OTHER PUBLICATIONS
Chemical Abstracts, vol. 79 (1973), p. 92235n.

Primary Examiner—V. D. Turner
Attorney, Agent, or Firm—Carl A. Cline

[57] ABSTRACT

Triazolylsulfonamides of a limited class are substantially non-phytotoxic and are useful as insecticides. For example 1-N,N-dimethylcarbamyl-3-tert.butyl-1,2,4-triazol-5-yl-N,N-dimethylsulfonamide is effective in aphid control, both by foliar application and systemically.

14 Claims, No Drawings

1-DIMETHYLCARBAMYL-3-BRANCHED ALKYL-1,2,4-TRIAZOL-5-YL-(N-SUBSTITUTED) SULFONAMIDES AND USE AS INSECTICIDES

This application is a continuation-in-part of copending U.S. Ser. No. 407,678, filed Oct. 18, 1973, now abandoned, which is incorporated herein by reference.

DESCRIPTION OF THE INVENTION

It is known that some carbamyltriazolylsulfonamides are useful as herbicides. However, we have discovered that substantially non-phytotoxic compounds which are extraordinarily effective as both systemic and contact insecticides are members of the class having the generic structural formula

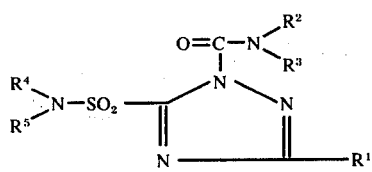

in which $R^1$ is $C_3$ to $C_4$ secondary or tertiary alkyl or cycloalkyl, $R^2$ is hydrogen or methyl, $R^3$ is methyl, $R^4$ is hydrogen, methyl or ethyl, $R^5$ is methyl or ethyl or $R^4$ and $R^5$ together may be azo, with the added provision that when $R^1$ is tert.butyl, $R^4$ may also be $C_3$ or $C_4$ alkyl or cycloalkyl, $R^5$ may also be $C_3$ or $C_4$ alkyl or cycloalkyl or phenyl or $R^4$ and $R^5$ together may also represent the remainder of a 3- to 6- membered ring structure, as for example, one of the following:

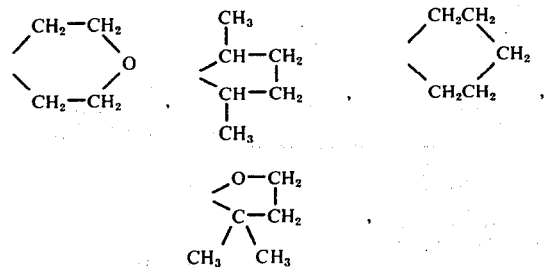

The nature of the substituent group $R^1$ appears to be particularly critical with respect to absence of phytotoxicity and efficacy as insecticides. The nature of the substituents, $R^4$ and $R^5$ also has an observable effect on insecticidal characteristics, both on contact and systemically.

Preferred compounds are those which are effective both systemically and by contact, as they are more versatile and more economical to use to combat chewing or sucking insects such as aphids. Particularly preferred compounds are those in which $R^1$ is tert.butyl. A laboratory method of preparation of these compounds from commercially available intermediates is as follows:

Preparation of 3-tert.butyl-4H-1,2,4-triazolin-5-thione

To a suspension of 50 g (0.55 mol) of thiosemicarbazide and 43 g (0.05 mol) of pyridine in 300 ml of dioxane was added 42.6 g (0.6 mol) of pivalyl chloride, with cooling. The reaction was stirred at room temperature for 72 hours, then poured into water. The resulting solid was collected, washed with water and dried. The unpurified pivalyl thiosemicarbazide was heated at reflux temperature in 300 ml of 10% sodium hydroxide solution for 3 hours. After cooling, the pH was adjusted to 4 with hydrochloric acid and the product collected, washed with water and dried to give 43.8 g, m.p. 200°–203°. Recrystallization from methanol chloroform gave a sample, m.p. 203°–205°.

Using a similar procedure, 3-isopropyl-4H-1,2,4-triazolin-5-thione, m.p. 194°–5°, was prepared.

The structural formula may be written in either the thiol or thione form, as shown in the outline of synthesis reactions below.

Synthesis of 3-tert.butyl-4H-1,2,4-thiazol-5-yl N,N-dimethylsulfonamide

This synthesis may be conveniently accomplished by means of two steps which are outlined as follows:

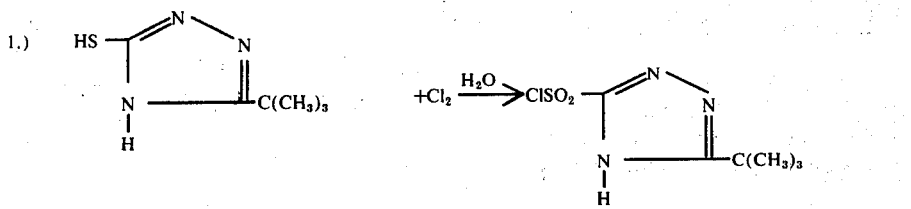

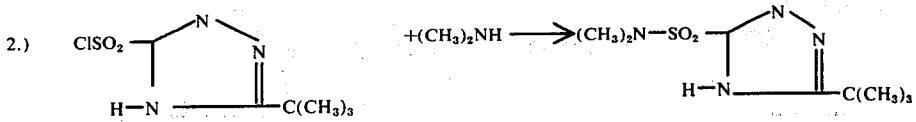

Reaction 1.

Chlorine gas is introduced through a fritted glass delivery tube beneath the surface of a stirred slurry of 50 g (0.32 mol) of 3-tert.butyl-4H-1,2,4-triazolin-5-thione in 450 ml water. The temperature of the reaction mixture is maintained at 0° to −10° by means of an ice-salt bath. When absorption of the chlorine is complete (about 76 g $Cl_2$) the slurry is filtered and the solid washed with water. When dry, the solid 3-tert.butyl-4H-1,2,4-triazol-5-yl sulfonyl chloride melts at 166°–168°. The solid is used while still slightly damp for the next step in the reaction sequence.

Reaction 2.

The entire product from reaction 1. is added in small portions to 72 g (0.64 mol) of 40% aqueous dimethylamine with stirring and cooling. The slurry is stirred one hour, then the solid is filtered and washed with water to give 46.0 g (62% yield) of 3-tert.butyl-4H-1,2,4-triazol-5-yl N,N-dimethylsulfonamide, m.p. 204°–207°.

By using similar procedures and various commercially available amines in Reaction 2. a great variety of compounds having structure II may be prepared.

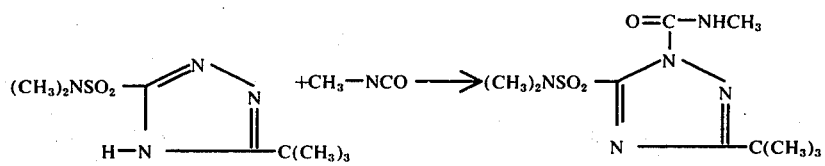

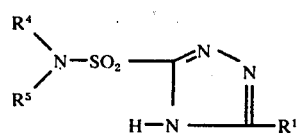

Specific examples of such compounds are listed below:

| R¹ | R⁴ | R⁵ | m.p. (°C) |
|---|---|---|---|
| (CH₃)₂CH— | CH₃ | CH₃ | 162–4° |
| (CH₃)₃C— | C₂H₅ | C₂H₅ | 158–60° |
| (CH₃)₃C— | C₂H₅ | H | 194–6° |
| (CH₃)₃C— | CH₃ | H | 205–7° |
| (CH₃)₃C— | H | H | 166–172° |
| (CH₃)₃C— | —CH₂—CH₂O—CH₂—CH₂— | | 229–231° |

Synthesis of 1-N,N-dimethylcarbamyl-3-tert.butyl-1,2,4-triazol-5-yl-N,N-dimethylsulfonamide (Compound No. 1)

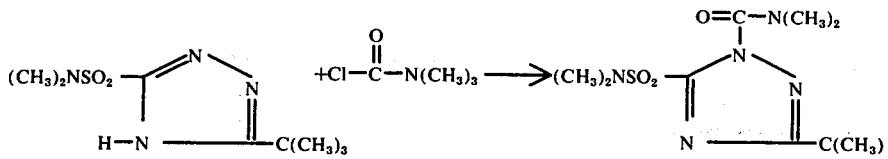

Dimethylcarbamyl chloride (3.4 g, 0.032 mol) is added slowly to a solution of 4.2 g (0.018 mol) of 3-tert.butyl-4H-1,2,4-triazol-5-yl N,N-dimethyl sulfonamide in 20 ml of benzene and 20 ml of pyridine. After refluxing overnight, the mixture is evaporated and the residue is partitioned between water and chloroform. The chloroform solution is evaporated and the residue partitioned between water and ether. Evaporation of the ether solution and recrystallization of the residue from hexane gives 1-N,N-dimethylcarbamyl-3-tert.butyl-1,2,4-triazol-5-yl-N,N-dimethylsulfonamide (compound No. 1) m.p. 108°–110°.

Synthesis of 1-N-methylcarbamyl-3-tert.butyl-1,2,4-triazol-5-yl-N,N-dimethylsulfonamide

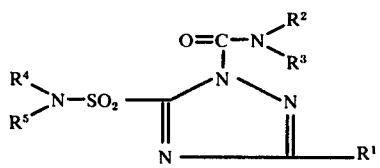

A solution of 8.0 g (0.034 mols) of 3-tert.butyl-4H-1,2,4-triazol-5-yl-N,N-dimethylsulfonamide and 3.4 g (0.06 mol) of methyl isocyanate in 20 ml of triethylamine is stirred overnight at room temperature. The solvent is evaporated under vacuum and the residue is slurried in water. The resultant solid is collected by filtration and recrystallized from ethanol to give 1-N-methylcarbamyl-3-tert.butyl-1,2,4-triazol-5-yl-N,N-dimethylsulfonamide, m.p. 193°–194.5°.

Using procedures of the type exemplified above, the following compounds represented by structural formula I were prepared, as listed below.

| COMPOUND | MELTING POINT (Deg. C.) |
|---|---|
| 1-N,N-dimethylcarbamyl-3-tert.butyl-1,2,4-triazol-5-yl-N,N-dimethyl-sulfonamide | 93–95 |
| 1-N,N-dimethylcarbamyl-3-tert.butyl-1,2,4-triazol-5-yl-N,N-(3-oxapentamethylene)sulfonamide | dec. 183–185 |
| 1-N,N-dimethylcarbamyl-3-tert.butyl-1,2,4-triazol-5-yl-N,N-diethylsulfonamide | 90–92 |
| 1-N,N-dimethylcarbamyl-3-tert.butyl-1,2,4-triazol-5-yl-sulfonamide | semi-solid |
| 1-N,N-dimethylcarbamyl-3-tert.butyl-1,2,4-triazol-5-yl-N-methylsulfon- | 162–165 |

-continued

| COMPOUND | MELTING POINT (Deg. C.) |
|---|---|
| amide | |
| 1-N-methylcarbamyl-3-tert.butyl-1,2,4-triazol-5-yl-N,N-diethylsulfonamide | 56–60 |
| 1-N,N-dimethylcarbamyl-3-tert.butyl-1,2,4-triazl-5-yl-N,N-pentamethylene-sulfonamide | 106–108 |
| 1-N,N-dimethyl-3-propyl-1,2,4-triazol-5-yl-N,N-dimethylsulfonamide | semi-solid |
| 1-N,N-dimethylcarbamyl-3-tert.butyl-1,2,4-triazl-5-yl-N-butyl-N-methyl-sulfonamide | semi-solid |
| 1-N,N-dimethylcarbamyl-3-isopropyl-1,2,4-triazol-5-yl-N,N-diethyl-sulfonamide | oil |
| 1-N,N-dimethylcarbamyl-3-tert.butyl-1,2,4-triazole-5-yl-N,N-(1,4-dimethyl-tetramethylene)sulfonamide | oil |
| 1-N,N-dimethylcarbamyl-3-tert.butyl-1,2,4-triazol-5-yl-N-propylsulfonamide | oil |
| 1-N,N-dimethylcarbamyl-3-tert.butyl-1,2,4-triazol-5-yl-N,N-(1-oxa-4,4-dimethyltetramethylene)sulfonamide | oil |
| 1-N,N-dimethylcarbamyl-3-tert.butyl-1,2,4-triazol-5-yl-N-phenylsulfonamide | oil |
| 1-N,N-dimethylcarbamyl-3-cyclo-propyl-1,2,4-triazol-5-yl-N,N-dimethylsulfonamide | 92–95 |
| 1-N,N-dimethylcarbamyl-3-cyclo-propyl-1,2,4-triazol-5-yl-N-ethylsulfonamide | oil |
| 1-N,N-dimethylcarbamyl-3-cyclo-propyl-1,2,4-triazol-5-yl-sulfonylazide | 63–67 |
| 1-N,N-dimethylcarbamyl-3-tert.butyl-1,2,4-triazol-5-yl-N-benzl-N-iso-propylsulfonamide | 126–127 |
| 1-N,N-dimethylcarbamyl-3-tert.butyl-1,2,4-triazol-5-yl-sulfonyl azide | oil |

The structure illustrated by structural formula I above corresponds to the chemical names assigned to the compounds listed above and is considered most likely correct for these compounds. The presence of two other possible isomeric structures represented by structural formulas III and IV cannot, however, be excluded.

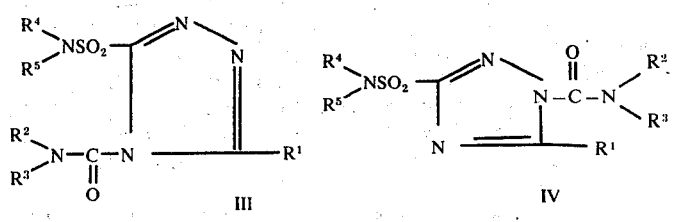

III IV

INSECTICIDAL USE

The insecticides listed above were employed in the killing of insects according to the following procedure, so as to obtain comparative data:

Two 5 oz. Dixie cups containing Henderson Dwarf lima bean plants and one 5 oz. Dixie cup containing Orange Gem nasturtiums, all growing in vermiculite, are placed on the turntable, and sprayed to thorough wetness with 25 ml of an aqueous dispersion of the candidate chemical at concentrations of 500, 250, 125, 62, 31 and 15 ppm. Nasturtiums were already infested with 50–100 bean aphids. The effects on aphids were judged by examination of the nasturtium plants 24 hours later and were rated according to the following schedule:

0 = none dead
1 = 1–25 percent dead
2 = 26–50 percent dead
3 = 51–75 percent dead
4 = 76–99+ percent dead
5 = 100 percent dead All of the compounds listed above gave a rating of 5 at concentrations of 500, 250 and 125 parts per million. All but seven also gave a rating of 5 at 62 parts per million concentration. All but six of the compounds on the list gave a rating of at least 4 at only 15 parts per million, indicating that they were capable of giving 1-N,N-dimethylcarbamyl-3-tert.butyl-1,2,4-triazol-5-yl-N-methylsulfonamide.
1-N-methylcarbamyl-3-tert.butyl-1,2,4-triazol-5-yl-N,N-diethylsulfonamide.
1-N,N-dimethylcarbamyl-3-tert.butyl-1,2,4-triazol-5-yl-N,N-pentamethylenesulfonamide.
1-N,N-dimethylcarbamyl-3-tert.butyl-1,2,4-triazol-5-yl-N-butyl-N-methylsulfonamide.
1-N,N-dimethylcarbamyl-3-tert.butyl-1,2,4-triazol-5-yl-N-propylsulfonamide.

When 20 ml. of aqueous dispersions of 1-N,N-dimethylcarbamyl-3-tert.butyl-1,2,4-triazol-5-yl-N,N-dime- satisfactory control with repeated spraying at this concentration level. The following compounds gave a rating of 5 (total kill), even at the lowest concentration (15 ppm) and are preferred aphicides on the basis of contact efficacy.

1-N,N-dimethylcarbamyl-3-tert.butyl-1,2,4-triazol-5-yl-N,N-dimethylsulfonamide.
1-N,N-dimethylcarbamyl-3-tert.butyl-1,2,4-triazol-5-yl-N,N-diethylsulfonamide.
1-N,N-dimethylcarbamyl-3-tert.butyl-1,2,4-triazol-5-yl-sulfonamide.

thylsulfonamide was applied at various concentrations to the soil in which plants were growing instead of the foliage, systemic aphicidal activity was demonstrated. This is shown in the table below, in which the same scoring system was used and Meta Systox R was included in the same experiment as a standard for comparison

| Concentration (ppm) | Score of Test Compound | Score of Meta Systox R |
|---|---|---|
| 50 | 5 | 5 |
| 10 | 5 | 5 |
| 1 | 4 | 5 |

The aqueous dispersions employed in the above illustrative examples were prepared by dissolving 25 mg. of aphicidal compound in 5 ml. of acetone and then diluting to the desired concentration with water containing 1.2 ml. of a commercial octylphenoxy polyethoxyethanol non-ionic surfactant (Triton X-100) per liter. By keeping surfactant concentration constant during dilution, dispersion is quick and the resulting homogeneous liquid has the appearance and behavior of a true solution. By spraying at a variety of concentrations, the efficacy of the aphicides is demonstrated and a standard is provided by means of which the skilled worker in the art can adjust the concentration to suit his needs. Water-dispersible solutions of the aphicides are readily prepared by conventional methods, employing non-phytotoxic commercially available emulsifiers, dispersing agents and auxiliary solvents. Other additives may be employed in formulations to reduce spray drift and aerosol formation, regulate viscosity and for other purposes, according to known practices.

In commercial use the aphicides are conveniently stored and shipped in the form of water-dispersible solutions or wettable powders and are diluted with water just prior to spraying. Because of the rather high efficacy of the compounds it is impractical to apply them uniformly to plants without some sort of carrier or diluent. Water is the preferred carrier or diluent but either or both solid and liquid diluents may be employed with the aphicides of this invention. The aphicides may be conveniently formulated as liquid emulsifiable concentrates or as emulsifiable powders according to representative procedures given below. All parts are parts by weight unless otherwise indicated.

| Wettable Powder | |
|---|---|
| Aphicide | 10 parts |
| Barden clay | 8 parts |
| Sodium dialkylnaphthalene sulfonate (75% active; Sellogen HR) | 1 part |
| Sodium-based lignin sulfonate dispersing agent (Polyfon H) | 1 part |

The resulting dry powder was easily dispersed in water to make up liquids for spray application.

Water Dispersible Concentrate

In a solvent mixture containing 257 parts of isophorone and 257 parts of mesityl oxide there was dissolved 40 parts of aphicidal compound, 30 parts of lipophilic emulsifier blend of anionic and nonionic surfactants (T-Mulz O) and 30 parts of a hydrophilic emulsifier blend of anionic and nonionic surfactants (T-Mulz W). The resulting liquid was a 6.5 percent active water-emulsifiable concentrate which was useful for preparing aqueous spray mixtures.

The aphicides of this invention may also be formulated according to conventional methods as oil sprays, microencapsulated powders, dusts and thickened aqueous sprays. The aphicides of the present invention need not be applied directly to the body of each insect, but only to the locus of the insects, that is, the place inhabited by the aphids, generally stems and foliage. Whether the aphids contact the aphicide during or after spraying is immaterial. Toxicity of the compounds to other types of insects, in general is relatively low, so that populations of predatory and competing species will remain established, even though plants are sprayed to obtain a substantially complete kill of aphids.

We claim:

1. The method of killing aphids on plants comprising applying to the plants a substantially non-phytotoxic but aphicidally effective amount of a compound having the generic structural formula

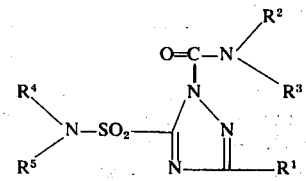

in which $R^1$ is $C_3$ to $C_4$ secondary or tertiary alkyl or cycloalkyl, $R^2$ is hydrogen or methyl, $R^3$ is methyl, $R^4$ is hydrogen, methyl or ethyl, $R^5$ is methyl or ethyl, with the added provision that when $R^1$ is tert.butyl, $R^4$ may also be $C_3$ or $C_4$ alkyl or cycloalkyl, and $R^5$ may also be $C_3$ or $C_4$ alkyl or cycloalkyl or phenyl.

2. The method of killing aphids on plants comprising applying to the plants a substantially non-phytotoxic but aphicidally effective amount of 1-N,N-dimethylcarbamyl-3-tert.butyl-1,2,4-triazol-5-yl-N,N-dimethylsulfonamide.

3. The method of killing aphids on plants comprising applying to the plants a substantially non-phytotoxic but aphicidally effective amount of 1-N,N-dimethylcarbamyl-3-tert.butyl-1,2,4-triazol-5-yl-N,N-diethylsulfonamide.

4. The method of killing aphids on plants comprising applying to the plants a substantially non-phytotoxic but aphicidally effective amount of 1-N,N-dimethylcarbamyl-3-tert.butyl-1,2,4-triazol-5-yl-sulfonamide.

5. The method of killing aphids on plants comprising applying to the plants a substantially non-phytotoxic but aphicidally effective amount of 1-N,N-dimethylcarbamyl-3-tert.butyl-1,2,4-triazol-5-yl-N-methylsulfonamide.

6. The method of killing aphids on plants comprising applying to the plants a substantially non-phytotoxic but aphicidally effective amount of 1-N-methylcarbamyl-3-tert.butyl-1,2,4-triazol-5-yl-N,N-diethylsulfonamide.

7. The method of killing aphids on plants comprising applying to the plants a substantially non-phytotoxic but aphicidally effective amount of 1-N,N-dimethyl-3-propyl-1,2,4-triazol-5-yl-N,N-dimethylsulfonamide.

8. The method of killing aphids on plants comprising applying to the plants a substantially non-phytotoxic but aphicidally effective amount of 1-N,N-dimethylcarbamyl-3-tert.butyl-1,2,4-triazol-5-yl-N-butyl-N-methylsulfonamide.

9. The method of killing aphids on plants comprising applying to the plants a substantially non-phytotoxic but aphicidally effective amount of 1-N,N-dimethylcarbamyl-3-isopropyl-1,2,4-triazol-5-yl-N,N-diethylsulfonamide.

10. The method of killing aphids on plants comprising applying to the plants a substantially non-phytotoxic but aphicidally effective amount of 1-N,N-dimethylcarbamyl-3-tert.butyl-1,2,4-triazol-5-yl-N-propylsulfonamide.

11. The method of killing aphids on plants comprising applying to the plants a substantially non-phytotoxic but aphicidally effective amount of 1-N,N-dimethylcarbamyl-3-tert.butyl-1,2,4-triazol-5-yl-N-phenylsulfonamide.

12. The method of killing aphids on plants comprising applying to the plants a substantially non-phytotoxic but aphicidally effective amount of 1-N,N-dimethylcarbamyl-3-cyclopropyl-1,2,4-triazol-5-yl-N,N-dimethylsulfonamide.

13. The method of killing aphids on plants comprising applying to the plants a substantially non-phytotoxic but aphicidally effective amount of 1-N,N-dimethylcarbamyl-3-cyclopropyl-1,2,4-triazol-5-yl-N-ethylsulfonamide.

14. The method of killing aphids on plants comprising applying to the plants a substantially non-phytotoxic but aphicidally effective amount of 1-N,N-dimethylcarbamyl-3-tert.butyl-1,2,4-triazol-5-yl-N-benzyl-N-isopropylsulfonamide.

* * * * *

PO-1050
(5/69)

UNITED STATES PATENT OFFICE
CERTIFICATE OF CORRECTION

Patent No. 3,973,028     Dated August 3, 1976

Inventor(s) William C. Doyle, Jr. and Joel L. Kirkpatrick

It is certified that error appears in the above-identified patent and that said Letters Patent are hereby corrected as shown below:

The specification, from line 55 in column 6 to line 11 in column 7 should read as follows:

satisfactory control with repeated spraying at this concentration level. The following compounds gave a rating of 5 (total kill), even at the lowest concentration (15 ppm) and are preferred aphicides on the basis of contact efficacy.

1-N,N-dimethylcarbamyl-3-tert.butyl-1,2,4-triazol-5-yl-N,N-dimethylsulfonamide.

1-N,N-dimethylcarbamyl-3-tert.butyl-1,2,4-triazol-5-yl-N,N-diethylsulfonamide.

1-N,N-dimethylcarbamyl-3-tert.butyl-1,2,4-triazol-5-yl-sulfonamide.

1-N,N-dimethylcarbamyl-3-tert.butyl-1,2,4-triazol-5-yl-N-methylsulfonamide.

1-N-methylcarbamyl-3-tert.butyl-1,2,4-triazol-5-yl-N,N-diethylsulfonamide.

1-N,N-dimethylcarbamyl-3-tert.butyl-1,2,4-triazol-5-yl-N,N-pentamethylenesulfonamide.

1-N,N-dimethylcarbamyl-3-tert.butyl-1,2,4-triazol-5-yl-N-butyl-N-methylsulfonamide.

1-N,N-dimethylcarbamyl-3-tert.butyl-1,2,4-triazol-5-yl-N-propylsulfonamide.

When 20 ml. of aqueous dispersions of 1-N,N-dimethylcarbamyl-3-tert.butyl-1,2,4-triazol-5-yl-N,N-dime- Signed and Sealed this Twelfth Day of October 1976

[SEAL]

Attest:

RUTH C. MASON
Attesting Officer

C. MARSHALL DANN
Commissioner of Patents and Trademarks